United States Patent [19]
Boyd et al.

[11] Patent Number: 5,491,147
[45] Date of Patent: Feb. 13, 1996

[54] TRI-SUBSTITUTED PHENYL DERIVATIVES AND THEIR USE IN PHARMACEUTICAL COMPOSITIONS AND METHODS OF TREATMENT

[75] Inventors: Ewan C. Boyd, Slough; Michael A. W. Eaton, Watlington; Graham J. Warrellow, Northwood, all of United Kingdom

[73] Assignee: Celltech, Limited, Slough, United Kingdom

[21] Appl. No.: 387,551

[22] Filed: Feb. 13, 1995

Related U.S. Application Data

[63] Continuation of Ser. No. 141,873, Oct. 22, 1993, abandoned.

[30] Foreign Application Priority Data

Oct. 23, 1992 [GB] United Kingdom .................. 9222253

[51] Int. Cl.$^6$ .................. A61K 31/50; A61K 31/505; C07D 239/26; C07D 237/08
[52] U.S. Cl. .................. 514/247; 514/256; 514/275; 544/224; 544/242; 544/335
[58] Field of Search .................. 514/247, 256; 275/277, 307, 311, 712, 717, 718; 544/224, 242, 335; 546/144, 173, 334, 339; 568/631, 642

[56] References Cited

U.S. PATENT DOCUMENTS

| | | | |
|---|---|---|---|
| 4,012,495 | 3/1977 | Schmiechen et al. | 424/274 |
| 4,015,017 | 3/1977 | Gazare | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,792,561 | 12/1988 | Walker et al. | 514/312 |
| 4,921,862 | 5/1990 | Walker et al. | 514/312 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |

FOREIGN PATENT DOCUMENTS

| | | |
|---|---|---|
| 0393500 | 10/1990 | European Pat. Off. ........... 544/224 |
| 0490823 | 6/1991 | European Pat. Off. . |
| 0470805 | 2/1992 | European Pat. Off. . |
| 0511865 | 11/1992 | European Pat. Off. . |
| 0537742 | 4/1993 | European Pat. Off. . |
| 2501443 | of 0000 | Germany . |
| 1588639 | 4/1981 | United Kingdom . |
| WO87/06576 | 11/1987 | WIPO . |
| WO91/15451 | 10/1991 | WIPO . |
| WO91/16892 | 11/1991 | WIPO . |
| WO92/00968 | 1/1992 | WIPO . |
| WO92/06963 | 4/1992 | WIPO . |
| 9206085 | 4/1992 | WIPO . |
| WO92/07567 | 5/1992 | WIPO . |
| WO92/19594 | 11/1992 | WIPO . |
| WO92/19602 | 11/1992 | WIPO . |
| WO93/19748 | 10/1993 | WIPO . |
| WO94/02465 | 2/1994 | WIPO . |
| WO94/12461 | 6/1994 | WIPO . |

OTHER PUBLICATIONS

Porter et al. Chem. Abstract, 117(9):90296w, 1992.
Ashton, "Selective Type IV Phosphodiesterase Inhibitors as Antiasthmatic Agents. The Syntheses and Biological Activities of 3-(Cyclopentyloxy)-4-methyoxybenzamides and Analogues" J. Med. Chem. 37:1696–1703 (1994).
Beavo & Reifsnyder, "Primary Sequence of Cyclic Nucleotide Phosphodiesterase Isozymes and the Design of Selective Inhibitors" TIPS 11:150–155 (1990).
Buu–Hoi, N. P. et al., "Bromination of Some 1,2, 2–Triarylethylenes" 1261–1263 (1958).
Buu–Hoi et al., "New Method for the Synthesis of ω,ω–Diarylacetophenones Aminated in the Aromatic Nucleus. Polynitration of Triarylethylenes" Chemical Abstracts 61:16006h (1964).
Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3, 1982.
El–Wakil et al., "Study of the proton magnetic resonance of methoxytamoxifen towards ortho–substitution" Chemical Abstracts 116:255248t (1992).

(List continued on next page.)

*Primary Examiner*—Yogendra N. Gupta
*Attorney, Agent, or Firm*—Woodcock Washburn Kurtz Mackiewicz & Norris

[57] ABSTRACT

Compounds of formula (1)

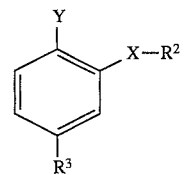

are described wherein Y represents a halogen atom or a group —OR$^1$, where R$^1$ is an optionally substituted alkyl group; R$^2$ represents an optionally substituted cycloalkyl or cycloalkenyl group; R$^3$ is a monocyclic or bicyclic aryl group optionally containing one or more heteroatoms selected from oxygen or sulphur atoms or a group —N(R$^4$)— where R$^4$ is a hydrogen atom or an alkyl group; X is —O—, —S—, or —N(R$^5$)—, where R$^5$ is a hydrogen or an alkyl group; with the proviso that when X is —O— then R$^3$ is not a 3-cyanamino-6-pyridazinyl or a 3-chloro-6-pyridazinyl group; and the salts, solvates, hydrates and N-oxides thereof.

The compounds are selective and potent inhibitors of phosphodiesterase IV and are useful for the prophylaxis and treatment of inflammatory diseases and the alleviation of conditions associated with central nervous malfunction.

21 Claims, No Drawings

OTHER PUBLICATIONS

Hirose et al., "Styrene Derivatives and Electrophotpgraphic Photoreceptor Containing Them" Chemical Abstracts 118:136183z (1993).

Ishikura, M. et al., "An Efficient Synthesis of 3–Heteroarylpyridines via Diethyl–(3–pyridyl)–borane" Synthesis pp. 936–938 (1984).

Manhas et al., "Heterocyclic Compounds XII. Quinazoline Derivatives as Potential Antifertility Agents(1)" J. Het. Chem: 711–715 (1979).

Mezheritskaya, "Synthesis and properties of carboxonium heterocyclic systems. VII. Synthesis and properties of 2–benzyl–substituted 1,3–dioxolanium salts" Chem. Abs. 93:95160j p. 635 (1980).

Mitsunobu, O., "The Use of Diethyl Azodicarboxylate and Triphenylphosphine in Synthesis and Transformation of Natural Products" Synthesis 1–28 (1981).

Nicholson et al., "Differential Modulation of Tissue Function and Therapeutic Potential of Selective Inhibitors of Cyclic Nucleotide Phosphodiesterase Isoenzymes" TIPS 12: 19–27 (1991).

O'Conner et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60(8) #10203.4 (Apr. 13, 1964).

Porter et al., "Preparation of 6–phenyl–3–(5–tetrazolyl)pyridin–2(H)–one Derivatives as Cyclic AMP–dependent Protein Kinase Agonists" Chem. Abstract 117(9):90296w (1992).

Ramalingam, Deshmukh and Sattur, "Synthesis and Pharmacology of 2,5–Disubstituted 1,3,4–Zxadiazoles" J. Indian Chem. Soc. vol. 58 (3) 269–271 (1981).

Reddy et al., "Inhibition of Breast Cancer Cell Growth in Vitro by a Tyrosine Kinase Inhibitor" Cancer Research 52:3636–3641 (1992).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29:1355–1362 (1986).

Seitz et al., "Fluorotamoxifen. A Caveat on the Generality of Electrophilic Destannylation" Chemical Abstracts 111:57136k (1989).

Sharp, M. J. et al., "Synthetic Connections to the Aromatic Directed Metalation Reaction. Functionalized Aryl Boronic Acids by Ipso Borodesilylation; General Synthesis of Unsymmetrical Biphenyls and n–Terphenyls" Tetrahedron Lett 28:5093–5097 (1987).

Thompson, W. J. and Gaudino, J., "A General Synthesis of 5–Arylnicotinates" J. Org. Chem. 49:5237–5243 (1984).

Yoneda et al., "The Antiproliferative Effects of Tyrosine Kinase Inhibitors Tyrphostins on a Human Squamous Cell Carcinoma in Vitro and in Nude Mice" Cancer Research 51:4430–4435 (1991).

TRI-SUBSTITUTED PHENYL DERIVATIVES AND THEIR USE IN PHARMACEUTICAL COMPOSITIONS AND METHODS OF TREATMENT

CROSS-REFERENCE TO RELATED APPLICATION

This application is a continuation of U.S. application Ser. No. 08/141,873, filed Oct. 22, 1993 now abandoned.

FIELD OF THE INVENTION

This invention relates to a novel series of tri-substituted phenyl derivatives, to processes for their preparation, to pharmaceutical compositions containing them, and to their use in medicine.

BACKGROUND TO THE INVENTION

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I-VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11:150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

A series of 3-cyanamino- and 3-chloro-(4-alkoxyphenyl)pyridazine compounds are described in European Patent Specification No. 393500. Certain of these compounds are claimed to have broncholoytic and anti-inflammatory activities.

SUMMARY OF THE INVENTION

We have now found a novel series of tri-substituted phenyl derivatives, members of which are potent inhibitors of PDE IV at concentrations at which they have little or no inhibitory action on other PDE isoenzymes. These compounds inhibit the isolated PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Certain other compounds are also able to modulate central nervous system (CNS) function. The compounds of the invention are therefore of use in medicine, especially in the prophylaxis and treatment of asthma, and for the alleviation of conditions associated with dementia and other CNS malfunctions.

Thus according to one aspect of the invention, we provide a compound of formula (1)

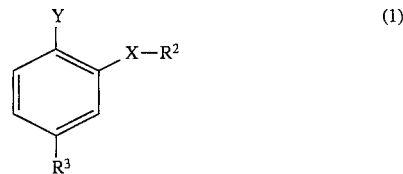

wherein

Y is a halogen atom or a group —OR$^1$, where R$^1$ is an optionally substituted alkyl group;

R$^2$ is an optionally substituted cyoloalkyl or oycloalkenyl group;

R$^3$ is a monocyclic or bicyclic aryl group optionally containing one or more heteroatoms selected from oxygen or sulphur atoms or a group —N(R$^4$)— where R$^4$ is a hydrogen atom or an alkyl group;

X is —O—, —S—, or —N(R$^5$)—, where R$^5$ is a hydrogen atom or an alkyl group;, with the proviso that when X is —O— then R$^3$ is not a 3-cyanamino-6-pyridazinyl or a 3-chloro-6-pyridazinyl group; and the salts, solvates, hydrates and N-oxides thereof.

In the compounds of formula (1), when Y is a halogen atom it may be for example a fluorine, chlorine, bromine or iodine atom.

When Y in the compounds of formula (1) is a group —OR$^1$, R$^1$ may be, for example, an optionally substituted straight or branched alkyl group, for example, an optionally substituted C$_{1-6}$alkyl group, (e.g. a C$_{1-3}$alkyl group), such as a methyl, ethyl, n-propyl, i-propyl, n-butyl, i-butyl, s-butyl, t-butyl, n-pentyl, i-pentyl, or n-hexyl group. Optional substitutents which may be present on R$^1$ groups include one or more halogen atoms, e.g. fluorine, chlorine, bromine or iodine atoms.

When R$^2$ in the compounds of formula (1) is an optionally substituted cycloalkyl or cycloalkenyl group it may be for example a C$_{3-8}$-cycloalkyl group such as a cyclobutyl, cyclopentyl, or cyclohexyl group or a C$_{3-8}$ cycloalkenyl group such as a cyclobutenyl, cyclopentenyl or cyclohexenyl group, each cycloalkyl or cycloalkenyl group being optionally substituted by one, two or three substituents selected from halogen atoms, e.g. fluorine, chlorine, bromine or iodine atoms, C$_{1-6}$alkyl e.g. C$_{1-3}$alkyl such as methyl or ethyl, hydroxyl or C$_{1-6}$alkoxy e.g. C$_{1-3}$alkoxy such as methoxy or ethoxy groups.

Monocyclic or bicyolic aryl groups represented by the group R$^3$ in compounds of formula (1) include for example $C_{6-12}$ optionally substituted aryl groups, for example optionally substituted phenyl or 1- or 2-naphthyl groups.

When the monocyclic or bicyclic aryl group contains one or more heteroatoms it may be for example a $C_{3-9}$ optionally substituted heteroaryl group containing for example one, two or three heteroatoms selected from oxygen or sulphur atoms or —N($R^4$)— groups. Examples of such groups include pyrrolyl, furanyl, thienyl, imidazolyl, oxazolyl, thiazolyl, pyrazolyl, pyridinyl, e.g. 2-, 3- or 4- pyridinyl, pyrimidinyl e.g. 5-pyrimidinyl, pyridazinyl e.g. 3-pyridazinyl or, 4-pyridazinyl, quinolinyl e.g. 4-quinolinyl, isoquinolinyl e.g. 4-isoquinolinyl, 5, 6, 7, 8-tetrahydroquinolinyl and 5, 6, 7, 8- tetrahydroisoquinolinyl. The heteroaryl group may be attached to the remainder of the molecule of formula (1) through any ring carbon or heteroatom as appropriate.

The aryl or heteroaryl groups represented by $R^3$ in compounds of formula (1) may each optionally be substituted by one, two, three or more substituents [$R^6$] selected from halogen atoms, e.g. fluorine, chlorine, bromine or iodine atoms, or $C_{1-6}$alkyl, e.g. methyl or ethyl, $C_{1-6}$alkoxy, e.g. methoxy or ethoxy, $C_{2-6}$alkylenedioxy, e.g. ethylenedioxy, $C_{5-7}$cycloalkoxy, e.g. cyclopentoxy, halo$C_{1-6}$alkyl, e.g. trifluoromethyl, $C_{1-6}$alkylamino, e.g. methylamino or ethylamino, $C_{1-6}$alkylthyl, e.g. methylthio, amino (NH$_2$), amino$C_{1-6}$alkyl, e.g. aminomethyl or aminoethyl, $C_{1-6}$dialkylamino, e.g. dimethylamino or diethylamino, nitro, cyano, hydroxyl (OH), carboxyl (CO$_2$H), —CO$_2$R$^6$ [where $R^6$ is a $C_{1-6}$alkyl e.g. methyl or ethyl, $C_{6-12}$aryl$C_{1-3}$alkyl, e.g. benzyl or phenethyl or $C_{6-12}$aryl, e.g. phenyl group], $C_{1-6}$alkanoyl e.g. acetyl, sulphonyl (—SO$_3$H), $C_{1-6}$alkyl-sulphonyl, e.g. methylsulphonyl, aminosulphonyl (—SO$_2$NH$_2$), $C_{1-6}$alkyl-aminosulphonyl, e.g. methylaminosulphonyl or ethylamino-sulphonyl, $C_{1-6}$dialkylaminosulphonyl, e.g. dimethylaminosulphonyl or diethyl..aminosulphonyl, carboxamido (—CONH$_2$), $C_{1-6}$alkylamino-carbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—NHSO$_2$H), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino $C_{1-6}$alkanoylamino, e.g. acetylamino, or $C_{1-6}$alkanoylamino$C_{1-6}$alkyl, e.g. acetylaminomethyl groups.

It will be appreciated that where two or more $R^6$ substituents are present, these need not necessarily be the same atoms and/or groups. The $R^6$ substituents may be present at any ring carbon atom away from that attached to the rest of the molecule of formula (1). Thus, for example, in phenyl groups represented by $R^3$ any substituent may be present at the 2-, 3-, 4-, 5- or 6- positions relative to the ring carbon atom attached to the remainder of the molecule.

When the groups —N($R^4$)— or —N($R^5$)— are present in the compounds of formula (1), $R^4$ and $R^5$ may each independently be a hydrogen atom or a $C_{1-6}$alkyl group such as a methyl or ethyl group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

One particular group of compounds of the invention has the formula (1) where $R^3$ is an unsubstituted monocyclic or bicyclic aryl group optionally containing one or more heteroatoms selected from oxygen or sulphur atoms or a group —N($R^4$)—, and Y, $R^2$, $R^3$, $R^4$ $R^5$ and X are as defined for formula (1).

Another group of compounds according to the invention has the formula (1) where $R^3$ is a monosubstituted monocyclic or bicyclic aryl group optionally containing a heteroatom selected from an oxygen or sulphur atom or a group —N($R^4$)—, and Y, $R^2$, $R^3$, $R^4$, $R^5$ and X are as defined for formula (1).

In the compounds of formula (1), the group Y is preferably an —OR$^1$ group, especially where $R^1$ is an optionally substituted $C_{1-3}$alkyl group, particularly an ethyl group or, especially, a methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula (2):

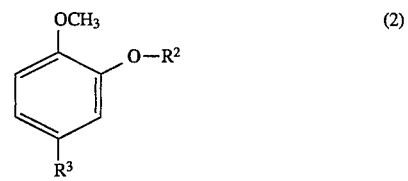

(2)

where $R^2$ is an optionally substituted cycloalkyl group; $R^3$ is as defined for formula (1) but is not a 3-cyanamino-6-pyridazinyl or a 3-chloro-6-pyridazinyl group; and the salts, solvates, hydrates and N-oxides thereof.

In the compounds of formulae (1) and (2) $R^2$ is preferably an optionally substituted cyclopentyl group. In particular, $R^2$ is a cyclopentyl group.

Particularly useful $R^3$ groups in compounds of formulae (1) and (2) include substituted phenyl groups, especially 3- and/or 4-substituted phenyl groups and naphthyl groups, especially 1-naphthyl. Particular groups of these types include 3-nitrophenyl, 3-methoxyphenyl, 4-methoxyphenyl, 3,4-dimethoxyphenyl and 3-cyclopentyloxy-4-methoxyphenyl.

Other particularly useful $R^3$ groups in compounds of formulae (1) and (2) include optionally substituted pyridinyl, particularly 3-pyridinyl and 4-pyridinyl, optionally substituted pyrimidinyl, especially 5-pyrimidinyl, and optionally substituted quinolinyl, 5, 6, 7, 8- tetrahydroquinolinyl, isoquinolinyl and 5, 6, 7, 8-tetrahydroisoquinolinyl, especially optionally substituted 3- or 4-quinolinyl, 4-isoquinolinyl and 5, 6, 7, 8-tetrahydroisoquinolin-4-yl. Optional substituents which may be present on these groups include, for example, amino and methyl groups. Particularly useful substituted groups of this type include 2-methylquinolin-4-yl and 1-aminoisoquinolin-4-yl.

A particularly useful group of compounds of the invention has the formula (1), especially the formula (2), wherein $R^3$ is an optionally substituted pyrimidinyl group, especially an optionally substituted 5-pyrimidinyl group.

A further particularly useful group of compounds of the invention has the formula (1), especially the formula (2) wherein $R^3$ is an unsubstituted or monosubstituted pyridinyl group, in particular a 3-pyridinyl, or, especially, a 4-pyridinyl group.

A still further particularly useful group of compounds of the invention has the formula (1), especially the formula (2) wherein $R^3$ is an optionally substituted isoquinolinyl group, in particular an optionally substituted 4-isoquinolinyl group.

Particularly useful compounds according to the invention are:

5-(3-Cyclopentyloxy-4-methoxyphenyl)pyrimidine;
4-(3-Cyclopentyloxy-4-methoxyphenyl) isoquinoline;
4-(3-Cyclopentyloxy-4-methoxyphenyl)pyridine;
2-Cyclopentyloxy-4-(3-cyclopentyloxy-4-methoxyphenyl)anisole;
4-(3-Cyclopentyloxy-4-methoxyphenyl-)-2-methylquinoline;
2-Cyclopentyloxy-4-(3-nitrophenyl)anisole;
4-(3-Cyclopentyloxy-4-methoxyphenyl)quinoline;
2-Cyclopentyloxy-4-(4-nitrophenyl)anisole;
4-(3-Cyclopentyloxy-4-methoxyphenyl)-2,3,5,6-tetrafluoropyridine;
5-Chloro-3-(3-cyclopentyloxy-4-methoxyphenyl)-2,4,6-trifluoropyridine;
5-(3-Cyclopentyloxy-4-methoxyphenyl)pyrimidine-2-carboxamide;

and the salts, solvates, hydrates and N-oxides thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm is present and where the elevation of cAMP levels may be expected to prevent or alleviate the inflammation and relax the muscle. Compounds according to the invention are also of particular use in the treatment of conditions associated with CNS malfunction.

Particular uses to which the compounds of the invention may be put include the prophylaxis and treatment of asthma, especially inflamed lung associated with asthma, or in the treatment of inflammatory airway disease, chronic bronchitis, eosinophillic granuloma, psoriasis and other benign and malignant proliferative skin diseases, endotoxic shock, septic shock, ulcerative colitis, Crohn's disease, reperfusion s injury of the myocardium and brain, inflammatory arthritis, chronic glomerulonephritis, atopic dermatitis, urticaria, allergic rhinitis, adult respiratory distress syndrome, diabetes insipidus, allergic conjunctivitis and vernal conjunctivitis.

Compounds according to the invention may also elevate cAMP in lymphocytes and thereby suppress unwanted lymphocyte activation in immune-based diseases such as rheumatoid arthritis, rheumatoid spondylitis, transplant rejection and graft versus host disease.

Compounds according to the invention may also be of particular use for the alleviation of conditions associated with dementia and other CNS malfunction for example in senile dementia (e.g. Alzheimer's disease), multiple infarct dementia and dementia caused by other agencies such as by brain tumours and by cerebral trauma.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or continuous infusion. Formulations for injection may be presented in unit dosage form e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispense device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10ng/kg to 50 mg/kg body weight for parenteral administration, and around 0.5 mg to around 1000 mg for nasal administration or administration by inhalation or insufflation.

The compounds according to the invention may be prepared by the following processes. The symbols Y, $R^2$, $R^3$ and X when used in the formulae below are to be understood to represent those groups described above in relation to formula (1) unless otherwise indicated.

Thus according to a further aspect of the invention, a compound of formula (1) may be prepared by coupling a boronic acid of formula (3)

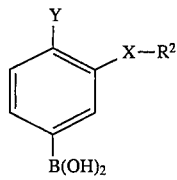

(3)

and a compound $R^3$-L (where L is a leaving group, for example a halogen atom such as a bromine or chlorine atom) in the presence of a complex metal catalyst. Suitable catalysts include heavy metal catalysts, for example palladium catalysts, such as tetrakis(triphenylphosphine) palladium. The reaction may be performed in an inert organic solvent, for example an aromatic hydrocarbon such as toluene or benzene, or an ether such as dimethoxyethane or dioxane, in the presence of a base, e.g. an alkali carbonate such as sodium carbonate, at an elevated temperature, e.g. the reflux temperature. In general, the metal catalyst and reaction conditions may be selected, depending on the nature of the boronic acid of formula (3) and/or the compound $R^3$-L, from a range of known alternatives for reactions of this type [see for example Miyaura, N et al, Synth. Commun. 1981, 11, 513; Thompson, W. J. and Gaudino, J., J. Org. Chem., 1984, 49, 5237 and Sharp, M. J. et al, Tetrahedron Lett., 1987, 28, 5093].

Intermediates $R^3$-L are either known compounds or may be prepared from known starting materials by methods analogous to those used for is the preparation of the known compounds. Thus, for example, where it is desired to obtain a compound $R^3$-L where L is a halogen atom such as a bromine or chlorine atom and this compound is not readily available, such a compound may be prepared by diazotisation of the corresponding amine using for example a nitrite such as sodium nitrite in an aqueous acid at a low temperature followed by reaction with an appropriate copper (I) halide in an aqueous acid.

Intermediate acids of formula (3) may be prepared by reaction of a halide of formula (4)

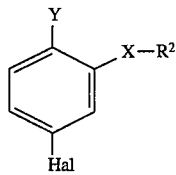

(4)

[where Hal is a halogen atom such as a bromine or chlorine atom] by halogen—metal exchange with a base such as n-butyl or t-butyl lithium followed by a borate such as triisopropylborate optionally at a low temperature e.g. around —70° C., in a solvent such as tetrahydrofuran.

Halides of formula (4) wherein X is —O—, —S— or —N($R^4$)— may be prepared by alkylation of a corresponding halide of formula (5)

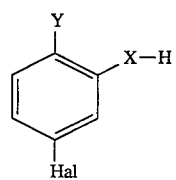

(5)

using a compound $R^2$Hal where [Hal is as just defined]0 where necessary in the presence of a base such as caesium or potassium carbonate or an alkoxide such as potassium t-butoxide, in a dipolar aprotic solvent such as an amide, e.g. a substituted amide such as dimethylformamide at ambient temperature or above e.g. around 40° C. to 50° C.

Intermediates of formula (5) where X is —O— may be prepared by oxidation of an aldehyde of formula (6)

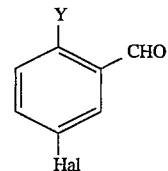

(6)

using an oxidising agent such as 3-chloroperoxybenzoic acid in a halogenated hydrocarbon such as chloroform at a temperature from around 0° C. to room temperature.

Aldehydes of formula (6) and halides of formula (5) where X is —S— or —N—($R^4$)— are either known compounds or may be prepared from known starting materials by methods analogous to those used for the preparation of the known compounds.

In another aspect of the invention a compound of formula (1) may be prepared by reaction of a halide of formula (4) with a borane $R^3$B(Alk)$_2$ (where Alk is a $C_{1-4}$alkyl group such as an ethyl group) or a boronic acid $R^3$B(OH)$_2$ using the reagents and conditions described above for the preparation of compounds of formula (1) from acids of formula (2) [see for example Ishikura, M et al, Synthesis, 1984, 936]. Intermediate boranes $R^3$B(Alk)$_2$ and boronic acids $R^3$B(OH)$_2$ for use in this process are either known compounds or may be prepared using methods analogous to those used for the preparation of the known compounds.

In yet another aspect of the invention, a compound of formula (1) may be prepared by alkylation of a compound of formula (7)

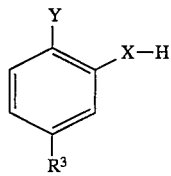

(7)

with a halide $R^2$Hal, as described above for the preparation of compounds of formula (4), or with an alcohol $R^2$OH, and a phosphine, such as triphenylphosphine, and an activator, for example diethyl azodicarboxylate, in the presence of an organic base such as triethylamine in a solvent such as tetrahydrofuran at an elevated temperature, e.g. the reflux temperature [see for example Mitsunobu, O., Synthesis., 1981, 1].

Intermediates of formula (7) may be prepared by reaction of a boronic acid of formula (3) wherein $R^2$ is a hydrogen atom with a compound $R^3$-L as described above for the preparation of compounds of formula (1) from acids of formula (3). In this reaction the group X-$R^2$ may need to be in a protected state. Conventional hydroxy, amino or thiol protecting groups may be used in accordance with standard practice [see, for example, Green, T. W. in "Protective Groups in Organic Synthesis" John Wiley and Sons, 1981].

According to a still further aspect of the invention a compound of formula (1) may be prepared by reaction of an intermediate halide of formula (4) by halogen-metal exchange with a base, for example a lithium base such as n-butyl or t-butyl lithium, followed by reaction with a compound $R^3H$, using for example the reagents and conditions described above for the preparation of Intermediates of formula (3) lo from Intermediates of formula (4).

Compounds of formula (1) may also be prepared by interconversion of other compounds of formula (1). Thus, for example, a compound of formula (1) where $R^3$ contains an amino (—$NH_2$) substituent may be prepared from a corresponding compound where $R^3$ contains a nitro group by reduction, using for example hydrogen in the presence of a metal such as platinum of palladium, optionally in the presence of an acid, such as acetic acid. Similar reduction conditions may also be used to convert a compound of formula (1) where $R^3$ is a quinolinyl or isoquinolinyl group to a corresponding compound where $R^3$ is a 5, 6, 7, 8-tetrahydroquinolinyl or 5, 6, 7, 8-tetrahydroisoquinolinyl group.

In another general example, a group represented by $R^3$ in compounds of formula (1) may be substituted by any of the groups $R^5$ by an appropriate addition or displacement reaction using the corresponding unsubstituted or substituted compound of formula (1) and a $R^5$ containing nucleophile or electrophile. Thus for example to obtain a group $R^3$ in compounds of formula (1) substituted by an amino (—$NH_2$) group, the corresponding unsubstituted compound may be reacted with an amide such as sodium amide in an inert solvent such as toluene, at an elevated temperature such as the reflux temperature. In another example, to obtain a group $R^3$ in compounds of formula (1) substituted by a cyano group, a corresponding compound containing a displaceable $R^5$ substituent, such as an alkylsulphonyl group, may be reacted with a nitrile such as potassium cyanide, at an elevated temperature. Similarly, compounds of formula (1) wherein $R^3$ contains an amino or alkoxy, e.g. methoxy, substituent may be prepared by treatment of a corresponding compound wherein $R^3$ contains a displaceable $R^5$ substituent with an alcoholic, e.g. methanolic, ammonia solution followed by separation of the desired amino and alkoxy compounds.

In another example of an interconversion process, a compound of formula (1) wherein $R^3$ contains a —$CH_2NH_2$ substituent may be prepared by reduction of a corresponding compound wherein $R^3$ contains a nitrile group, using for example a complex metal hydride such as lithium aluminium hydride in a solvent such as an ether e.g. diethylether.

In a further example, a compound of formula (1) wherein $R^3$ contains an alkanoylamino or alkanolyaminoalkyl substituent may be prepared by acylation of a corresponding compound wherein $R^3$ contains a —$NH_2$ or alkylamino group by reaction with an acyl halide in the presence of a base, such as a tertiary amine e.g. triethylamine in a solvent such as dichloromethane.

In yet another example of an interconversion process, a compound of formula (1) wherein $R^3$ contains an alkylsulphonyl substituent may be prepared by oxidation of a corresponding compound wherein $R^3$ contains an alkylthio group using for example an oxidising agent such as a peroxy acid, e.g. 3-chloroperoxybenzoic acid, in an inert solvent such as a halogenated hydrocarbon, e.g. dichloromethane, at a low temperature, e.g. below 10° C.

In a still further example of an interconversion process according to the invention, a compound of formula (1) wherein $R^3$ contains a carboxamido (—$CONH_2$) substituent may be prepared by oxidation of a corresponding compound where $R^3$ contains a cyano substituent, using an oxidising agent, for example hydrogen peroxide and a base such as sodium hydroxide in a solvent such as an alcohol, e.g. ethanol. N-oxides of compounds of formula (1) may be prepared by oxidation of the corresponding nitrogen base using an oxidising agent such as hydrogen peroxide in the presence of an acid such as acetic acid, at an elevated temperature, for example around 70° C. to 80° C., or a peroxyacid such as 3-chloroperoxybenzoic acid in a solvent such as a halogenated hydrocarbon, e.g. dichloromethane, at e.g. room temperature.

Salts of compounds of formula (1) may be prepared by reaction of a compound of formula (1) with an appropriate acid or base in a suitable solvent using conventional procedures.

DESCRIPTION OF SPECIFIC EMBODIMENTS

The following examples illustrate the invention.

The following abbreviations are used:

| | |
|---|---|
| DMF | dimethylformamide |
| THF | tetrahydrofuran |
| DME | dimethoxyethane |
| EtOAc | ethyl acetate |
| $Et_2O$ | diethylether |
| RT | room temperature |
| t.l.c. | thin layer chromatography |

INTERMEDIATE 1

5Bromo-2-methoxyphenol

A solution of 5-bromo-2-methoxybenzaldehyde (100 g, 0.46 mol) in chloroform (250 ml) was cooled with an ice bath and 3-chloroperoxybenzoic acid (50–60% purity) (146 g, 0.51 mol) in chloroform (1000 ml) added. The reaction mixture was allowed to warm slowly to room temperature and stirred for 72 h. The white solid was filtered off and the filtrate concentrated in vacuo. The residue was dissolved in ether (200 ml) and washed with 1M sodium sulphite solution (2×200 ml) then sodium hydrogen carbonate [half saturated] (3×200 ml). The ether layer was washed with 10% aqueous sodium hydroxide (3×100 ml) and the combined basic extract was acidified with concentrated hydrochloric acid and extracted with $Et_2O$ (3×100 ml). The combined organic extract was dried ($MgSO_4$) and florisil (10 g) filtered and the solvent removed under reduced pressure to give the title compound (90g) as a pale brown solid.

INTERMEDIATE 2

4-Bromo-2-cyclopentyloxyanisole

Intermediate 1 (90 g)was dissolved in DMF (300 ml), and treated with $Cs_2CO_3$ (158 g, 490 mmol), and cyclopentylbromide (73 g, 52.5 ml, 490 mmol). After stirring overnight, $Cs_2CO_3$ (35 g, 107 mmol), and cyclopentylbromide (12 ml, 16.7 g, 112 mmol) were added and stirring continued for 2h. A further portion of cyclopentylbromide (10 ml) and $Cs_2CO_3$ (14 g) were then added. After stirring for 1 h, the DMF was evaporated in vacuo and the residue diluted with water (200 ml) and extracted with $Et_2O$ (3×100 ml). The combined organic extract was washed with NaOH solution (5%, 2×100 ml), water (100 ml), then dried ($MgSO_4$) and the solvent evaporated in vacuo to give a red oil which was distilled (140° C., 0.3 mbar) to afford the title compound (101 g) as a colourless oil Found: C, 53.11; H, 5.53. $C_{12}H_{15}BrO_2$ requires C, 53.15; H, 5.58%.

INTERMEDIATE 3

3-Cyclopentyloxy,4-methoxyphenylboronic acid

To a stirred solution of Intermediate 2 (8.0 g, 29.5 mmol) in dry THF (60 ml), at −70° C. under an argon atmosphere was added n-butyllithium (1.45M, 23.4 ml, 33.9 mmol) over 10 minutes. After stirring for a further 30 minutes triisopropylborate (11.10 g, 13.6 ml, 59 mmol) was added at such a rate that the temperature did not exceed −60° C. The reaction mixture was stirred at −60° C. for 10 mins then the cooling removed and the reaction allowed to warm to room temperature (20 mins). After stirring for 2 h the reaction was quenched with 10% aqueous HCl solution and stirred for 0.5 h. The reaction mixture was extracted with EtOAc (3×40 ml) and the combined organic extract washed with brine (100 ml), dried ($MgSO_4$) and the solvent removed in vacuo. The resulting white solid was heated to reflux in $Et_2O$/hexane 1:3 then cooled to room temperature and the product filtered off. The filtrate was concentrated in vacuo and the residue flash column chromatographed [$SiO_2$; EtOAc/hexane, 1:9 (500 ml), then 1:1 (500 ml)] to afford a second crop. Total yield of the title compound was 5.23 g (m.p. 175°–177° C.). $\delta_H H(CDCl_3; 80MHz)$ 1.6–2.1 (8H, br m, $(CH_2)_4$), 3.90 (3H, s, OMe), 4.89 (1H, br m, $OCHCH_2$), 6.95 (1H, d, J8.0Hz, ArH ortho to OMe), 7.65–7.85 (2H, m, 2xArH meta to OMe).

INTERMEDIATE 4

5-Bromoisoquinoline

To a cold (0° C.) solution of HBr-$H_2O$ (48%) (10 ml) in water (30 ml) was added 5-aminoisoquinoline (5 g; 35 mmol) followed by sodium nitrite (2.4 g; 35 mmol) in water (20 ml). The mixture was added to a warm (75° C.) solution of cuprous bromide (5 g; 35 mmol) in HBr-$H_2O$ (48%) (50 ml) and stirred overnight at 75° C. The reaction mixture was cooled, basified to pH11 with NaOH (5M) and steamed distilled to afford the title compound (1.4 g) as a colourless crystalline solid (mp 65° C.).

INTERMEDIATE 5

2-Methylthiopyrimidine

To a solution of potassium hydroxide (12 g) in methanol (30 ml) was added 2-mercaptopyrimidine (20 g). The mixture was stirred to achieve total solubility before adding methyl iodide (25.36 g) while keeping the temperature of the reaction below 30° C. with an ice-bath cooling. The stirring was maintained for 2 h at RT before removing the solvent in vacuo. The slurry was extracted with $Et_2O$ (500 ml), filtered and the solution evaporated to afford a pale yellow oil. Filtration through a silica pad ($Et_2O$/hexane, 1:1) gave, after evaporation, the title compound (21 g) as a colourless oil. $\delta_H(CDCl_3;)$ 2.55 (3H, s, $CH_3$), 6.94 (1 H, t, pyrimidine $H_5$), 8.46 (2H, d, J4.8Hz, pyrimidine $H_4$, $H_6$).

INTERMEDIATE 6

5Bromo-2-Methylthiopyrimidine

A reaction mixture containing Intermediate 5 (10 g), and bromine (12.7 g) in carbon tetrachloride (200 ml) and in 1,2-dichloroethane (100 ml) was heated to gentle reflux for 3 days. The reaction mixture was poured into aqueous sodium sulphite (20%; 100 ml) and stirred until the orange colour had largely disappeared. The pH was adjusted to 7 with 20% NaOH and the aqueous phase extracted with dichloromethane (3×100 ml). The combined organic phase was washed with brine (50 ml), dried ($MgSO_4$) and evaporated to give an oil. Flash chromatography [$SiO_2$; 10% $Et_2O$/hexane] gave the title compound as an off-white solid (mp 63°–65° C.).

EXAMPLE 1 a)  5-(3-Cyclopentyloxy-4-methoxyphenyl)pyrimidine hydrochloride

To a stirred solution of tetrakis(triphenylphosphine) palladium[O] (0.59 g, 0.51 mmol) in DME (150 ml) at room temperature under an argon atmosphere was added 5-bromopyrimidine (3.24 g, 20.4 mmol). After stirring for 20 minutes sodium carbonate (2M, 20.4 ml) was added followed by Intermediate 3 (4.0 g, 17 mmol). The mixture was immediately refluxed for 16 h then poured into half saturated NaCl solution (100 ml). EtOAc (50 ml) was added and the organic phase separated. The aqueous portion was extracted with EtOAc (100 ml) and the combined organic extract washed with brine, dried over $MgSO_4$ and the solvent evaporated in vacuo to yield a clear oil. Flash column chromatography [$SiO_2$; $Et_2O$/hexane; 1:1 (1000 ml) then 7:3 (1000 ml)] furnished the title compound free base (4.49 g) as a white crystalline solid.

Treatment of the base with ethanolic HCl afforded the title compound as a pale yellow solid [m.p. 131°–147° C. (dec)]. Found: C, 62.33; H, 6.29; N, 9.03. $C_{16}H_{18}N_2O_2$·HCl requires C, 62.64; H, 6.24; N, 9.13%. $\delta_H(CDCl_3; 80MHz)$ 1.6–2.1 (8H, br m, $(CH_2)_4$), 3.90 (3H, s, OMe), 4.87 (1 H, br m, $OCHCH_2$), 7.0–7.25 (3H, m, 1xortho and 2xmeta ArH to OMe), 9.23 (2H, s, pyrimidine $H_4$, $H_6$), 9.28 (1 H, s, pyrimidine $H_2$), 10.60 (1 H, br s, NH).

The following compounds were prepared in a manner similar to the compound of Example 1 a).

b)  2-Chloro-5-(3-Cyclopentyloxy-4-methoxyphenyl)pyrimidine

From Intermediate 3 (1.04 g) and 5-bromo-2-chloropyridine (1.0 g). Flash column chromatography [$SiO_2$; EtOAc/hexane, 1:9 then 2:8 then 2.5:7.5] yielded the title compound (1.02 g) as a white crystalline solid (mp 88°–90° C.). Found: C, 63.10; H, 5.62; N, 9.15. $C_{16}H_{17}ClN_2O_2$ requires C, 63.05; H, 5.62; N, 9.19%.

c)  4-(3-Cyclopentyloxy-4-methoxyphenyl)-2,3.5.6-tetrafluoropyridine

From Intermediate 3 (1.01 g) and 4-bromo-2,3,5–6-tetrafluoropyridine (1.181 g). Column chromatography [$SiO_2$; EtOAc] followed by recrystallisation from hexane furnished the title compound (1.184 g)as an off-white powder (mp 115°–116° C.). Found: C, 59.84; H, 4.55; N, 3.81. $C_{17}H_{15}NO_2F_4$ requires C, 59.83; H, 4.43; N, 4.10%.

d) 5-Chloro.-3-(3-Cyclopentyloxy-4-methoxyphenyl)-2,4,6-trifluoropyridine

From Intermediate 3 (1.085 g) and 3,5-dichloro-2,4,6-trifluoropyridine (1.13 g). Column chromatography [$SiO_2$; dichloromethane] furnished the title compound (1.125 g) as a white flaky powder (mp 100°–102° C.). Found: C, 57.14; H, 4.30; N, 3.83; Cl, 10.05. $C_{17}H_{15}ClF_3NO_2$ requires C, 57.07; H, 4.23; N, 3.92; N, 3.92; Cl, 9.91%.

e)  5-(3-Cyclopentyloxy-4-methoxyphenyl)-2-methylthio pyrimidine

From Intermediate 3 (1.04 g) and Intermediate 6 (1.06 g). Flash column chromatography [$SiO_2$; $Et_2O$/hexane, 1:2) furnished the title compound (550 mg) as a white crystalline solid (mp 84.5°– 86.5° C.). Found C, 64.47; H, 6.25; N, 8.74. $C_{17}H_{20}N_2O_2S$ requires C, 64.55; H, 6.32; N, 8.86%.

f) 1-(3-Cyclopentyloxy-4-methoxyphenyl)naphthalene

From Intermediate 3 (0.50 g) and 1-bromonaphtalene (0.526 g). Column chromatography [SiO$_2$; EtOAc/hexane, gradient elution] gave the title compound (0.485 g) as colourless crystals (mp 123°– 125° C.). Found C, 82.45; H, 6.96. C$_{22}$H$_{22}$O$_2$ requires C, 82.99; H, 6.96.

EXAMPLE 2

4-(3-Cyclopentyloxy-4-methoxyphenyl)isoquinoline

To DME (15 ml) filtered through alumina under nitrogen was added tetrakis(triphenylphosphine) palladium[O] (51 mg, 0.044 mmol) and 4-bromoisoquinoline (304 mg, 1.46 mmol). The reaction mixture was stirred at room temperature for 20 min before adding aqueous sodium carbonate solution (2M, 1.46 ml) and Intermediate 3 (300 mg, 1.27 mmol). The mixture was immediately heated to reflux. After 16 h the reaction mixture was poured into water (50 ml) and extracted with Et$_2$O (3×40 ml). The organic extract was washed with brine (50 ml), dried (MgSO$_4$), and the solvent removed under reduced pressure. The crude oil was subjected to flash chromatography (Et$_2$O/hexane, 2:3 then 3:2) to afford the title compound (396 mg) as a colourless oil, $\delta_H$(CDCl$_3$; 80MHz) 1.6–2.1 (8H, br m, (CH$_2$)$_4$), 3.91 (3H, s, OMe), 4.77 (1H, br m, O CHCH$_2$), 6.99 (3H, s, 1xortho and 2xmeta ArH to OMe), 7.5–7.7 (2H, m, isoquinoline H$_6$, H$_7$), 7.85–8.1 (2H, m, isoquinoline H$_5$, H$_8$), 8.43 (1H, s, isoquinoline H$_3$), 9.17 (1 H, s, isoquinoline H$_1$). m/z 319 (M$^+$, 30%), 252 (35), 251 (M$^+$-cyclopentyl, 100), 237 (12), 236 (63), 208 (20), and 190 (11).

Treatment of the oil with ethereal HCl/ethanol afforded the hydrochloride salt as a pale yellow solid, [m.p. 171°–186° C.(dec) (from acetone)]. Found: C, 70.83; H, 6.19; N. 3.82. C$_{21}$H$_{21}$NO$_2$.HCl requires C, 70.88; H, 6.23; N, 3.94%.

EXAMPLE 3 a) 4-(3-Cyclopentyloxy-4-methoxyohenyl)pyridine hydrochloride

Tetrakis(triphenylphosphine) palladium [0] (5 mol %, 89 mg) was added to a solution of 4-bromopyridine hydrochloride (1.54 mol, 0.30 g) in DME (filtered through Grade 1 Alumina, 50 ml) and the mixture stirred under dry nitrogen for 15 minutes. Intermediate 3 (0.40 g, 1.69 mmol) was added as a solid followed by sodium carbonate solution (2M, 1.54 ml) and then a further portion of sodium carbonate (0.1 g). The mixture was immediately heated to reflux. After 16 h, the mixture was cooled, diluted with Et$_2$O (150 ml) and brine (100 ml), the organic layer was separated, dried (Na$_2$SO$_4$) and concentrated in vacuo to give a brown oil. The oil was subjected to flash chromatography [Et$_2$O/EtOAc (100:0 to 50:50)] to yield the title compound free base (0.260 g) as a pale yellow solid.

Treatment of the base with ethanolic-ethereal HCl afforded the title compound as a white solid (m.p. 213°–222° C.) (dec). Found: C, 66.39; H. 6.54; N, 4.49. C$_{17}$H$_{19}$NO$_2$.HCl requires C, 66.77; H, 6.59; N, 4.58%), $\delta_H$(CDCl$_3$; 80MHz) 1.6–2.1 (8H; br m, (CH$_2$)$_4$), 3.92 (3H, s, OMe), 4.85 (1H, br m, OCHCH$_2$), 6.99 (1H, d, J 8.6Hz, ArH ortho to OMe), 7.23 (1H, d, J2.3Hz, ArH ortho to cyclopentyloxy), 7.38 ( 1H, dd, J8.4, 2.3 Hz, ArH para to cyclopentyloxy), 8.01 (2H, d, J7.0 Hz, pyridine H$_3$, H$_5$), 8.75 (2H, d, J7.0Hz, pyridine H$_2$, H$_6$); m/z 269 (M$^+$-HCl, 43%), 202 (67), 201 (M$^+$-HCl-cyclopentyl, 187 (28), 186 (95), 183 (19), 158 (47), 69 (12), 41 (57), and 36 (43).

The following compounds were prepared in a similar manner to the compound of Example 38):

b) 2-(3-Cyclopentyloxy-4-methoxyphenyl)toluene from Intermediate 3 (367 mg) and 2-bromotoluene (293 mg) to yield the title compound (241 mg) as a colourless oil. Found: C, 80.67; H, 7.75. C$_{19}$H$_{22}$O$_2$ requires C, 80.82; H, 7.85%. m/z 282 (M$^+$, 16%), 215 (15), 214 (M$^+$-cyclopentyl, 100), 200 (11), 199 (32), 181 (15), 153 (12), 124 (24), 109 (11) and 28 (27).

c) Methyl 3-(3-Cyclopentyloxy-4-methoxyphenyl)benzoate from Intermediate 3 (430 mg) and methyl 3-bromobenzoate (356 mg) to yield the title compound (300 mg) as a colourless oil, $v_{max.}$ (neat) 2960, 1725, 1520, 1450, 1250, 805, 755cm$^{-1}$. $\delta_H$(CDCl$_3$; 80MHz) 1.5–2.1 (8H, br m, (CH$_2$)$_4$), 3.83 (3H, s, OMe), 3.89 (3H, s, OMe), 4.83 (1H, br m, OCHCH$_2$), 6.86 (IH, d, J9Hz, ArH ortho to OMe), 6.9–7.2 (2H, m, 2xArH meta to OMe), 7.44 (1H, d, J7.5Hz, ArH meta to CO$_2$Me), 7.66 (1 H, ca, dt, J7.5, 1.5Hz, ArH para to CO$_2$Me), 7.91 (1 H, ca.dt, J7.5, 1.5Hz, ArH para to aryl), 8.17 (1 H, ca.t, J1.5Hz, ArH ortho to CO$_2$Me and aryl); m/z 326 (M$^+$, 10%), 259 (16), 258 (M$^+$-cyclopentyl, 100), 244 (9), 243 (54), 215 (17) and 41 (9).

d) 4-(4-Chlorophenyl)-2-(cyclopentyloxy)anisole from Intermediate 3 (300rag) and 4-bromochlorobenzene (292 mg) to yield the title compound (213 mg) as a white solid [m.p. 88°– 91° C. (from hexane)]. Found: C, 71.74; H, 6.30. C$_{18}$H$_{19}$ClO$_2$ requires C, 71.40; H, 6.32%.

e) 2-Cyclopentyloxy-4-(3-methoxyphenyl)anisole from Intermediate 3 (1.01 g) and 3-bromoanisole (800rag) to yield the title compound (350 mg) as a white amorphous powder. Found: C, 76.51; H, 7.46. C$_{19}$H$_{22}$O$_3$ requires C, 76.48; H, 7.43%) $\delta_H$(CDCl$_3$; 80MHz) 1.5–2.1 (8H, br m (CH$_2$)4), 3.83 (3H, s, OMe), 3.85 (3H, s, OMe), 4.81 (1H, br m, OCHCH$_2$), 6.7–7.4 (7H, m, ArH); m/z 298(M$^+$, 31%), 231 (15), 230 (M$^+$-cyclopentyl 100), 215 (38), 200 (11), 187 (14) and 41 (14).

f)  2-Cyclopentyloxy-4-(3-cyclopentyloxy-4-methoxyohenyl) anisole from Intermediate 3 and Intermediate 2 to yield the title compound as pale yellow flakes. Found: C, 75.11; H, 7.81. C$_{24}$H$_{30}$O$_4$ requires C, 75.36; H, 7.91%.

g) 2-Cyclopentyloxy-4-(4-nitrophenyl)anisole from Intermediate 3 (300 mg) and 1-bromo-4-nitrobenzene (300mg) to yield the title compound (400 mg) as yellow needles, [m.p. 119°–120° C. (hexane)]. Found: C, 69.09; H, 6.02; N, 4.45. C$_{18}$H$_{19}$NO$_4$ requires C, 69.00; H, 6.11; N, 4.47%) $\delta_H$(CDCl$_3$; 80 mHz) 1.6–2.1 (8H, m, (CH$_2$)$_4$), 3.88 (3H, s, OMe), 4.83 (1H, br m, OCHCH$_2$), 6.85–7.20 (3H, ArH ortho to OMe and 2xArH meta to OMe), 7.62 (2H, dm, J ca. 9Hz, 2xArH meta to NO$_2$); 8.22(2H, dm, Jca. 9Hz, 2xArH ortho to NO$_2$); m/z 313 (M$^+$, 5%), 246 (15), 245 (M$^+$-cyclopentyl, 100), 230 (49), 149 (21), and 83 (15).

h) 4.( 3-Cyanophenyl)-2-(cyclopentyloxy)anisole from Intermediate 3 (500 mg) and 3-bromobenzonitrile (440 mg) to yield the title compound (610 mg) as a white solid, [m.p. 70°–71° C. (hexane-toluene)]. Found: C, 77.72; H, 6.51; N, 4.80. C$_{19}$H$_{19}$NO$_2$ requires C, 77.79; H, 6.53; N, 4.77%) $\delta_H$(CDCl$_3$; 80 mHz) 1.6–2.1 (8H, br m, (CH$_2$)$_4$), 3.84 (3H, s, OMe), 4.83 (1 H, br m, OCHCH$_2$), 6.85–7.15 (3H, m ArH ortho and 2xArH meta to OMe), 7.2–7.8 (4H, m, 2xArH ortho and 2xArH meta and ArH para to CN); m/z 293 (M$^+$, 6%), 226 (16), 225 (M$^+$-cyclopentyl, 211 (9), 210 (60), and 182 (17).

i) 2-(3-Cyclopentyloxy-4-methoxyohenyl)-5-nitropyridine from Intermediate 3 (300 mg) and 2-bromo-5-nitropyridine (297 mg) to afford the title compound (405 mg) as a pale yellow solid, [m.p. 110°–111° C. (diisopropyl ether)]. Found: C, 64.99; H, 5.74; N, 8.89. C$_{17}$H$_{18}$N$_2$O$_4$ requires C, 64.96; H, 5.74; N, 8.89 $\delta_H$ (CDCl$_3$; 80 mHz) 1.5–2.1 (8H, br m, (CH$_2$)$_4$), 3.90 (3H, s, OMe), 4.90 (1 H, br m, OCHCH$_2$), 6.92 (1 H, d, J8.5Hz, ArH ortho to OMe), 7.58 (1 H̄, dd, J8.3, 2.0Hz, ArH para to OMe), 7.70 (1 H, d, J1.4Hz, ArH ortho to cyclopentyloxy), 7.76 (1 H, d, J8.7Hz, ArH meta to NO$_2$), 8.40 (1 H, dd, J8.8, 2.5Hz, pyridine H$_4$), 9.37 (1 H, d, J2.5Hz, pyridine H$_2$); m/z 314 (M$^+$, 14%), 247 (26), 246 (M$^+$-cyclopentyl,100), 231 (54), 203 (12), 173 (11), 41 (11) 32 (15) and 28 (58).

j) 2-(3-Cyclopentyloxy-4-methoxyohenyl)thiophene from Intermediate 3 (300 mg) and 2-bromothiophene (238 mg) to afford the title compound (345 mg) as white needles [(m.p. 67°– 68° C.) (hexane)]. Found: C, 69.96; H, 6.67. C$_{16}$H$_{18}$O$_2$S requires C, 70.04; H, 6.61%; δ$_H$(CDCl$_3$; 80 mHz) 1.5–2.1 (8H, br m, (CH$_2$)$_4$), 3.83 (3H, s, OMe), 4.80 (1 H, br m, OCHCH$_2$), 6.80 (1 H, d, J8.7Hz, ArH ortho to OMe), 6.9–7.2 (5H, m, 2xArH meta to OMe), and thiopone H$_3$, H$_4$, H$_5$); m/z 274 (M$^+$, 24%), 207 (13), 206 (M$^+$-cyclopentyl, 100), 192 (10), 191 (85), 163 (18), and 41 (12).

k) 5-(3-Cyclopentyloxy-4-methoxyphenyl)isoquinoline from Intermediate 3 (228 mg) and Intermediate 4 (202 mg) to afford the title compound (299 mg) as a white crystalline solid [m.p. 115°– 116° C. (acetone)]. Found: C, 78.71; H, 6.62; N, 4.30. C$_{21}$H$_{21}$NO$_2$ requires C, 78.97; H, 6.63; N, 4.39% δ$_H$(CDCl$_3$; 80 mHz) 1.5–2.1 (8H, br m, (CH$_2$)$_4$), 3.90 (3H, s, OMe), 4.75 (1 H, br m, OCHCH$_2$), 6.96 (3H, s, ArH ortho and 2xArH meta to OMe), 7.55–8.05 (4H, m, isoquinoline H$_4$, H$_6$, H$_7$, H$_8$), 8.44 (1 H, d, J5.8Hz, isoquinoline H$_3$) and 9.23 (1 H̄, s isoquinoline H$_1$) m/z 319 (M$^+$, 24%), 252 (32), 251 (M$^+$-cyclopentyl, 236 (55), 209 (13), 208 (13), 135 (49), and 77 (10).

l) 2-(3-Cyclopentyloxy-4-methoxyphenyl)pyridine from Intermediate 3 (423 mg; 1.79 mmol) and 2-bromopyridine (325 mg; 2.06 mmol), to yield the title compound (0,475 g) as a white crystalline solid [m.p. 74°–75° C. (n-hexane)]. δ$_H$(CDCl$_3$) 1.6– 2.1 (8H, br m, (cH$_2$)$_4$, 3.87 (3H, S, OMe), 4.91 (1H, br m, OCHCH$_2$), 6.90 (1 H, d, J8.4Hz, ArH ortho to OMe), 7.0–7.2 (1 H, m, ArH), 7.47 (1 H̄, dd, J8.4, 2.1HZ, ArH para to OCp), 7.55–7.7 (3H, m, ArH) and 8.59 (1H, dm, J4.7Hz, ArH ortho to pyN); m/z 269 (M$^+$, 11%), 202 (15), 201 (M$^+$-Cp, 100), 186 (56), 158 (16), 32 (13), and 28 (53).

Treatment of the title compound with ethereal HCl afforded the hydrochloride salt as a yellow solid [.m.p. 167°–170° C. (dec) (from ether/ethanol)]. Found: C, 66.67; H, 6.62; N, 4.54. C$_{17}$H$_{19}$NO$_2$ HCl requires C, 66.77; H, 6.59; N, 4.58%.

m) 2-(3-Cyclopentyloxy-4-methoxyphenyl)benzonitrile

From Intermediate 3 (1.016 g) and 2-Bromobenzonitrile (0,965 g). Column chromatography [SiO$_2$; dichloromethane] furnished the title compound (1.175 g) as colourless oil. Found: C, 77.00; H, 6.52; N. 4.54. C$_{19}$H$_{19}$NO$_2$ requires C, 77.52; H, 6.85; N, 4.76%.

EXAMPLE 4

3-(3-Cyclopentyloxy-4-methoxyphenyl)pyridine hydrochloride

A solution of Intermediate 2 (2.812 g, 10.37 mmol) in DME (filtered through Al$_2$O$_3$) (25 ml) was treated with tetrakis(triphenylphosphine) palladium[O] (0.36 g, 0.31 mmol) and stirred at RT for 0.25 h. Diethyl(3-pyridyl)borane (1.50 g, 10.20 mmol) and sodium carbonate [(2.2 g, 20.7 mmol) in 10 ml H$_2$O] was added and the mixture heated to reflux for 5 h. The mixture was cooled and partitioned between EtOAc (50 ml) and brine (30 ml). The organic layer was separated and combined with a further EtOAc wash (25 ml). The organic extract was washed (brine; 20 ml), dried (Na$_2$SO$_4$), and concentrated in vacuo to yield a yellow oil which was subjected to flash column chromatography (SiO$_2$:Et$_2$O-hexane; 1:1) to give a pale yellow oil (2.14 g). The oil was dissolved in ethanol and treated with Et$_2$O-HCl until the title compound just began to precipitate. The mixture was stored at 4° C. for 72 h, then the product was collected by filtration, washed with Et$_2$O and dried in vacuo to yield the title compound (1.76 g) as white needles. Found: C, 66.61; H, 6.60; N, 4.47. C$_{17}$H$_{19}$NO$_2$.HCl requires C, 66.77; H, 6.59; N, 4.58%). m/z 269 (M$^+$-HCl, 26%), 202 (34), 201 (M$^+$-HCl-cyclopentyl, 100%), 187 (16), 186 (93), 158 (30).

EXAMPLE 5

4-(3-Cyclopentyloxy-4-methoxyphenyl)-2-methylquinoline hydrochloride hemihydrate A solution of 4-chloroquinaldine (2.25 g, 12.7 mmol) in dioxane (20 ml) was treated with tetrakis(triphenylphosphine) palladium[O] (440 mg, 0.38 mmol) and stirred at RT for 0.5 h. Intermediate 3 (3.00 g, 12.71 mmol) and Na$_2$CO$_3$ [(2.7 g, 25.4 mmol) in ml H$_2$O] was added and the mixture heated to reflux for 18 h. The mixture was cooled and diluted with EtOAc (50 ml) and brine (25 ml). The organic phase was separated and combined with a further EtOAc extract (50 ml). The extract was washed (brine; 25 ml), dried (Na$_2$SO$_4$), and concentrated in vacuo to give a pale brown oil which was flash column chromatographed (SiO$_2$; Et$_2$O-hexane; 1:1) to give a colourless oil which crystallised to give a white solid on standing (3.78 g). The solid (0.5 g) was dissolved in ethanol-HCl then diluted with Et$_2$O to the crystallising point. The mixture was allowed to stand in the refrigerator for 48 h, then the supernatant was removed by decantation. The residue was washed with ether then dried in vacuo to afford the title compound as a yellow solid. δ$_H$(CDCl$_3$; 80MHz) 1.5–2.1 (8H, m (CH$_2$)$_4$), 3.19 (3H, s, ArMe), 3.94 (3H, s, OMe), 4.79 (1H, br m, OCHCH$_2$), 7.01 (1H̄, s, ArH), 7.05 (2H, s, ArH), 7.44 (1H, s, quinoline H$_3$), 7.6–8.2 (4H, m, quinoline H$_5$, H$_6$, H$_7$, H$_8$), 8.99 (1 H̄, d, J8.0Hz, NH). m/z 333(M$^+$-HCl, 12%), 266 (19), 265 (M$^+$-HCl-cyclopentyl, 100%) 250 (19), and 222 (15).

EXAMPLE 6

1-Amino-4-(3-Cyclopentyloxy-4-methoxyphenyl)isoquinoline hydrochloride

To a solution of the compound of Example 2 (1.0 g, 3.13 mmol) in dry toluene (20 ml) under nitrogen at room temperature was added a 50% wt suspension of sodium amide in toluene (estimated excess) and this heated to reflux overnight. The reaction mixture was quenched cautiously with water (40 ml) and allowed to stir under nitrogen for 10 mins before pouring into brine (40 ml) and extracting with EtOAc (3×40 ml). The organic extract was washed with brine (60 ml), dried (MgSO$_4$) and the solvent removed in vacuo. The brown oily residue, was subjected to flash chromatography [EtOAc, hexane, 1:3 (500 ml); 1:1 (500 ml) the EtOAc with 2 ml of concentrated NH$_3$ (1000 ml)] to yield an off-white solid (598 mg) which was dissolved with heating in propan-2-ol and precipitated with diisopropyl ether to afford a pale brown powder (290 mg). The powder was treated with ethereal HCl/ethanol to yield the title compound as an off-white solid. [m.p. 253°–257° C. (dec.)]. Found C, 67.63; H, 6.23; N, 7.55. C$_{21}$H$_{23}$N$_2$O$_2$.HCl requires C, 68.01; H, 6.25; N, 7.55%. m/z 334 (M$^+$-HCl, 46%), 266 (M$^+$-HCl-cyclopentyl, 100).

EXAMPLE 7

2-Cyclopentyloxy-4-(3-nitrophenyl)anisole i) A mixture of Intermediate 1 (2.50 g) and 3-nitrobenzeneboronic acid (3.10 g) was coupled using the Suzuki conditions exemplified in Example 1 to afford 2-cyclopentyloxy-4-(3-nitrophenyl)phenol (1.0 g) as yellow plates.

ii) 2-Cyclopentyloxy-4-(3-nitrophenyl)phenol (600 mg, 2.45 mmol) was dissolved in DMF (40 ml) and treated with $Cs_2CO_3$ (730 mg, 2.24 mmol) and cyclopentyl bromide (0.32 ml, 2.94 mmol). After stirring overnight at RT some of the phenol remained ($SiO_2$:t.l.c, $CH_2Cl_2$). $Cs_2CO_3$ (870 mg, 2.67 mmol) and cyclopentyl bromide (0.32 ml, 2.94 mmol) were added. After stirring at RT for 3 h the phenol had been consumed. The reaction mixture was filtered and concentrated in vacuo. The residue was dissolved in $Et_2O$ (50 ml), filtered, and concentrated in vacuo to give a yellow solid which was recrystallised from dichloromethane/hexane to afford the title compound (378 mg) as yellow needles. $\delta_H$(CDCl$_3$; 80 mHz) 1.5–2.1 (8H, br m, (CH$_2$)$_4$), 3.87 (3H, s, OMe), 4.84 (1H, br m, OCHCH$_2$), 6.91 (1 H, d, J9.1Hz, ArH ortho to OMe), 7.0–7.2 (2H, m, ArH meta to OMe), 7.54 (1H, d, J7.5Hz, ArH meta to NO$_2$), 7.80 (1 H, ca. dt, Jca 7.5, 1.5Hz, ArH para to NO$_2$), 8.09 (1 H, ca. dt, J ca.8, 1.5Hz, ArH para to aryl), 8.33 (1 H, ca. t, J ca 2Hz, ArH ortho to NO$_2$ and aryl); m/z 313 (M$^+$, 7%), 246 (17), 245 (M$^+$-cyclopentyl, 100), 230 (41 ), 202 (8), and 139 (9).

EXAMPLE 8

4-(3-Cyclopentyloxy-4-methoxyphenyl)quinoline

A solution of 4-chloroquinoline (2.08 g; 12.71 mmol) in dioxane (30 ml) was treated with tetrakis (triphenylphosphine)palladium (0) (440 mg; 0.38 mmol) and stirred at room temperature for 0.5 hr. Intermediate 3 (3 g; 12.71 mmol) and Na$_2$CO$_3$ (2.7 g; 25.4 mmol) in H$_2$O (12 ml) (ca 2M) were added and the mixture heated to reflux for 18 hr. The reaction mixture was diluted with EtOAc (50 ml) and brine (25 ml) and the organic layer separated. The aqueous layer was re-extracted with EtOAc (50 ml) and the combined organic layer was washed with brine (20 ml), dried (Na$_2$SO$_4$) and concentrated in vacuo to give a pale brown oil (4.91 g). The crude oil was dissolved in Et$_2$O-hexane (1:1), and the resulting precipitate collected by filtration, washed with hexane and dried in vacuo to afford the title compound as a white solid. Found C, 78.80; H, 6,56; N, 4.30. C$_{21}$H$_{21}$NO$_2$ requires C, 78.97; H, 6.63; N, 4.39%. $\delta_H$(CDCl$_3$) 1.5–2.0 (8H, m, (CH$_2$)$_4$), 3.91 (3H, s, OMe), 4.76 (1H, br m, OCHCH$_2$), 6.99 (3H, s, ArH), 7.27 (1H, D, J4.7Hz, quinoline H$_3$), 7.4–7.7 (2H, m, quinoline H, H), 7.9–8.2 (2H, m, quinoline H, H) and 8.86 (1 H, d, J4.5 Hz, quinoline H$_2$).

Dissolution of the title compound (0.5 g) in ethanolic HCl followed by dilution with ether afforded the hydrochloride salt (0.63 g) as a yellow powder. Found C, 70.79; H, 6.14; N, 3.9. C$_{21}$H$_{21}$NO$_2$ HCl requires C, 70.88; N, 6.23; N, 3.94%. $\delta_H$(CDCl$_3$) 1.5–2.1 (8H, m, (CH$_2$)$_4$), 3.95 (3H, s, OMe), 4.81 (1 H, br m, OCH CH$_2$), 7.09 (3H, br s, ArH), 7.7–8.3 (5H, m, quinoline H$_3$, H$_5$, H$_6$, H$_7$, H$_8$), 8.88 (1 H, d, J8.5Hz, quinoline H$_2$) and 9.01 (1 H, br s, NH)

EXAMPLE 9

4-(3-Cyclopentyloxy-4-methoxyphenyl)-5,6,7,8,-tetrahydroisoquinoline

To a solution of the compound of Example 2 (0.5 g; 1.57 mmol) in glacial acetic acid (20 ml) was added platinum (IV) oxide (0.1 g; 0.04 mmol). The reaction mixture was purged with N$_2$ and stirred for 60 h under a hydrogen atmosphere. The reaction mixture was filtered through celite and the filter washed through with acetic acid (2×10 ml). The filtrate and washings were poured slowly into saturated sodium carbonate solution (100 ml) and extracted with EtOAc (3×60 ml). The combined organic phase was washed with saturated hydrogen carbonate (2×100 ml) and brine (100 ml), dried (MgSO$_4$) and the solvent removed in vacuo. Purification by column chromatography yielded the title compound (88 mg) $\delta_H$ (CDCl$_3$) 1.5–2.1 (12H, br m, OCH(CH$_2$)$_4$+CH$_2$(CH$_2$)$_2$CH$_2$), 2.5–2.9 (4H, br m, CH$_2$(CH)$_2$CH$_2$), 3.85 (3H, s, OMe), 4.75 (1 H, br m, OCHCH$_2$), 6.7–6.95 (3H, m, ArH ortho+ 2 x meta to OMe), 8.17 (1H, s, isoquinoline H$_1$ or H$_3$) and 8.22 (1 H, s, isoquinoline H$_1$ or H$_3$).

Treatment of the title compound with ethereal HCl afforded the hydrochloride salt as a yellow crystalline solid (mp 189°–191° C.). Found C, 69.66; H, 7.36; N. 3.83. C$_{21}$H$_{25}$NO$_2$. HCl requires C, 70.08; H, 7.28; N, 3.89%- m./z 323 (M$^+$, 15), 256 (22), 255 (M$^+$-Cp,100), 240 (M$^+$-Cp-Me, 28), 170 (13), 141 (12), 36 (16), 32 (14), 28 (54).

EXAMPLE 10

5-( 3-Cyclopentyloxy-4-methoxyphenyl)pyrimidine-N-oxide

A solution of 5-(3-Cyclopentyloxy-4-methoxyphenyl)pyrimidine (1.37 g) and 3-chloroperoxybenzoic acid (50.60%) (1.75 g) in dichloromethane (35 ml) was stirred at RT and the reaction followed by t.l.c. After 5 days, the reaction mixture was partitioned three times between dichloromethane (50 ml) and 10% aqueous Na$_2$SO$_3$ solution (50 ml). The combined organic phase was washed with 5% aqueous NaOH solution (3×30 ml), brine (30 ml), dried (MgSO$_4$) and evaporated to afford a tan solid. Flash chromatography [SiO$_2$; dichloromethane/EtOAc, 1:9 then dichloromethane/EtOAc/methane, 1:8:1] followed by recrystallisation from EtOAc furnished the title compound (390 g) as a white powder (mp 140°–143° C.). Found=C, 67.03; H, 6.31; N, 9.81. C$_{16}$H$_{18}$N$_2$O$_3$ requires C, 67.12; H, 6.34; N, 9.78%.

EXAMPLE 11 a) 3-(3-Cyclopentyloxy-4-methoxyphenyl)pyridazine
b) 4-(3-Cyclopentyloxy-4-methoxyphenyl)pyridazine To a stirred solution of Intermediate 2 (3 g) in dry THF (30 ml) at −70° C. under an argon atmosphere was added n-butyllithium (1.6M in hexanes) (7.95 ml) over 15 min. The reaction mixture was stirred at −70° C. for 15 mins, neat pyridazine (0.96 ml) was then added and the mixture allowed to warm slowly (ca. 1 h) to room temperature. The solution was quenched with 5% aqueous acetic acid solution (5 ml) then partitioned several times between EtOAc and water. The combined organic phase was washed with aqueous NaHCO$_3$, brine, dried (MgSO$_4$) then concentrated in vacuo to yield a dark oil (2.8 g). Flash chromatography [SiO$_2$; 2% methanol/dichloromethane] gave two fractions containing the two title compounds.

Recrystallisation (from EtOAc/hexane (1:3)) of the first fraction, followed by suspension in hot Et$_2$O, cooling and filtration furnished 3-( 3-cyclopentyloxy-4-methoxyphenyl)pyridazine (260 mg) as a pale yellow fluffy crystalline solid (mp 112°–114° C.). Found C, 70.99; H, 6.69; N, 10.20. C$_{16}$H$_{18}$N$_2$O$_2$ requires C, 71.09; H, 6.71; N, 10.36%.

Recrystallisation from EtOAc/hexane (1:5), of the second fraction followed by flash chromatography [SiO$_2$; 1% methanol/dichloro methane] then recrystallisation from (EtOAc/hexane, 1:4) furnished 4-( 3-Cyclopentyloxy-4-methoxyphenyl) pyridazine (200 mg) as pale yellow needles(mp 100°–102° C.). Found C, 71.16; H, 6.70; N, 10.17. C$_{16}$H$_{18}$N$_2$O$_2$ requires C, 71.09; H, 6.71; N, 10.36%.

EXAMPLE 12

5-(3-Cyclopentyloxy-4-methoxyphenyl)-2-methylsulphonyl pyrimidine

To a cold (0° C.) solution of the compound of Example 1e (5.82 g) in dichloromethane (100 ml) was added solid 3-chloroperoxybenzoic acid in batches. The temperature was kept below 10° C. and the stirring carried on for 1 h. The precipitate was filtered off and washed with dichloromethane (4×50 ml). The combined organic extract was washed with 10% aqueous Na$_2$SO$_3$ (2×50 ml), saturated aqueous NaHCO$_3$ (3×50 ml), brine (50 ml), dried (MgSO$_4$) and evaporated in vacuo. Flash chromatography [SIOC$_2$; Et$_2$O/hexane, 1:4] followed by recrystallisation from EtOAc furnished the title compound (3.7 g) as a white solid (mp 188°–190° C.). Found C, 58.39; H, 5.76; N, 8.06. C$_{17}$H$_{20}$N$_2$O$_4$S requires C, 58.60; H, 5.79; N, 8.04%.

EXAMPLE 13 a) 2-Amino-5-(3-cyclopentyloxy-4-methoxyohenyl) pyrimidine
b) 5-(3-Cyclopentyloxy-4-methoxyphenyl)-2-methoxy pyrimidine A solution of the compound of Example 12 (1.0 g) in 2M ammonia and methanol (2.88 ml) in dichloromethane (5 ml) was stirred for 2 days. Ammonia solution (3 ml) was added and the reaction mixture stirred at room temperature for a further 6 days. The solvent was removed in vacuo and the residue purified by flash chromatography [SIO$_2$; 2% methanol, dicholoromethane then 5% methanol/dichloromethane] to give two fractions containing the two title compounds.

Concentration in vacuo of the first fraction gave a white crystalline solid which was recrystallised from methanol/hexane to furnish 5-(3-cyclopentyloxy-4-methoxyphenyl)-2-methoxy pyrimidine (380 mg) as a white fluffy solid (mp 91°–93° C.). Found C, 68.05; H, 6.64; H, 9.23. C$_{17}$H$_{20}$N$_2$O$_3$ requires C, 67.98; H, 6.71; N, 9.33%.

Concentration in vacuo of the second fraction gave a white solid. Recrystallisation from EtOAc/hexane ( 1:1 ) furnished 2-amino-5-(3-cyclopentyloxy-4-methoxyphenyl)pyrimidine as a white crystalline powder (50 mg) (mp 167°–169° C.). Found C, 67.25; H, 6.77; N, 14.66. C$_{16}$H$_{19}$N$_3$O$_2$ requires C, 67.35; H, 6.71; N, 14.73%

EXAMPLE 14

5-(3-Cyclopentyloxy-4-methoxyphenyl)-2-pyrimidine carbonitrile

To a solution of potassium cyanide (205 mg) in dry DMF (10 ml) was added the compound of Example 12 (1.0 g) and the reaction mixture stirred at room temperature for 3 hr then at 50° C. for 2 h. The reaction mixture was poured into a saturated NaHCO$_3$ solution (2.5 g Na$_2$CO$_3$ in 120 ml ice). The resulting yellow precipitate was filtered off and washed with water. Recrystallisation from EtOAc/hexane (1:2) gave the title compound (575 mg) as yellow needles (mp 121°–123° C.). Found C, 69.15; H, 5.73; N, 14.13. C$_{17}$H$_{17}$N$_3$O$_2$ requires C, 69.14; H, 5.80; N, 14.23%.

EXAMPLE 15

5-(3-Cyclopentyloxy-4-methoxyphenyl)pyrimidine-2-carboxamide

To a stirred mixture of the compound of Example 14 (1.3 g) in ethanol (8 ml) was added hydrogen peroxide (40 vols, 15 ml) and 6M aqueous NaOH (6 ml). After 15 min, the reaction mixture was diluted with water (75 ml) and the white solid filtered off. Recrystallisation from acetonitrile furnished the title compound (200 g) as small white plates (mp235°–238° C.). Found C, 65.06; H, 6.09; N, 13.44. C$_{17}$H$_{19}$N$_3$O$_3$ requires C, 65.16; H, 6.11; N, 13.41%.

The activity and selectivity of compounds according to the invention was demonstrated in the following tests.

1. Isolated Enzyme

The potency and selectivity of the compounds of the invention was determined using a battery of distinct PDE isoenzymes as follows:

i. PDE I, rabbit heart ii. PDE II, rabbit heart iii. PDE III, rabbit heart iv. PDE IV, HL60 cells.

The enzymes were purified to kinetic homogeneity using standard chromatographic techniques.

Phosphodiesterase activity was assayed as follows. The reaction was conducted in 150 µl of standard mixture containing (final concentrations): 50 mM TES-NaOH buffer (pH 7.5), 10 mM MgCl$_2$, 0.1 µM [$^3$H]-cAMP and vehicle or various concentrations of the test compounds. The reaction was initiated by addition of enzyme and conducted at 30° C. for between 5 to 30 mins. The reaction was terminated by addition of 50 µl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention were able to inhibit the action of the PDE IV HL60 enzyme at concentrations at which they had little or no effect on the action of each of the other PDE isoenzymes. Thus, compounds of the Examples have approximate Ki values (Ki PDEIV HL60 at 1 µM) in the nM-µM range, for example the compounds of Examples 2, 4 and 7 have approximate Ki values of 180 nM, 270nM and 250nM respectively.

2. The Elevation of cAMP in Leukocvtes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds induced a concentration-dependent elevation of cAMP in neutrophils and/or eosinophils at concentrations of 1 nM to 1 µM.

3. Suppression of Leukocyte Function

Compounds of the invention were investigated for their effects on superoxide generation and chemotaxis of human neutrophils. Neutrophils were separated from peripheral blood, incubated with dihydrocytochalasin B for superoxide generation only and test compound prior to stimulation with FMLP. The most potent compounds caused a concentration-dependent inhibition of superoxide generation and chemotaxis at concentrations of 0.1 nM to 1 μM.

4. Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenated Krebs' solution. The smooth muscle was contracted with submaximal concentrations of histamine or carbachol prior to the addition of increasing concentrations of test compound to the organ baths. The most potent compounds caused a concentration-dependent reversal of both histamine and carbachol-induced contractions at concentrations of 1 nM to 100 μM. The compounds were generally more potent in reversing histamine-induced tone than carbachol-induced tone.

5. Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors such as rolipram do not have any direct effects whereas selective PDE III inhibitors such as milrinone have positive chronotropic and inotropic effects. The non-specific PDE inhibitor theophylline, which is used in asthma as a bronchodilator, also causes significant cardiovascular changes such as tachycardia. Selective PDE IV inhibitors have advantage over theophylline, therefore, through reduced cardiovascular side effects. The most potent and selective compounds of the invention had no direct effects on the atrial and papillary muscles in vitro at concentrations up to 100 μM but in combination with PDE III inhibitors, these inhibitors showed an enhancement of chronotropic and inotropic activity, typical of selective type IV inhibitors.

6. Anti-allergic Activity in vivo

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the invention (0.1–10 mg/kg i.p.), up to three times during the 48 h following antigen challenge, lead to a significant reduction in the eosinophilia and the accumulation of other inflammatory leukocytes. There was also less inflammatory damage in the lungs of animals treated with compounds of the invention.

7. Effects on Pulmonary Dynamics

Compounds of the invention have been tested for their effects on ozone-induced hyperreactivity of the airways of guinea pigs. Following the inhalation of ozone, guinea pigs become very much more sensitive to the bronchoconstrictor effects of inhaled histamine than naive animals. There is a pronounced shift to the left (10–30 fold) of the dose response curve to histamine and a highly significant increase in the maximum increase in pulmonary resistance. Compounds of the invention administered 1 h prior to ozone by the intraperitoneal (0.01–1 mg/kg) or oral (0.1–10 mg/kg) route caused a dose-dependent inhibition of ozone-induced hyperreactivity.

In general, in our tests above, compounds of the invention have had no observed toxic effects when administered to animals at the doses shown.

We claim:

1. A compound of formula (1)

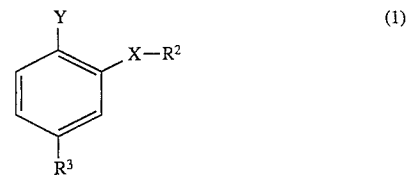

wherein:

Y is halogen or —OR$^1$, where R$^1$ is substituted or unsubstituted C$_{1-6}$alkyl, said R$^1$ substituent being halogen;

R$^2$ is substituted or unsubstituted C$_{3-8}$cycloalkyl or substituted or unsubstituted C$_{3-8}$cycloalkenyl, said R$^2$ substituents being halogen, C$_{1-6}$alkyl, hydroxyl or C$_{1-6}$alkoxy;

R$^3$ is substituted or unsubstituted pyrimidinyl or substituted or unsubstituted pyridazinyl, said R$^3$ substituents being C$_{1-6}$alkyl; C$_{1-6}$alkoxy; C$_{2-6}$alkylenedioxy; C$_{5-7}$cycloalkoxy; haloC$_{1-6}$alkyl; C$_{1-6}$alkylthio; nitro; carboxyl (—CO$_2$H) and carboxyl esterified by C$_{1-6}$alkyl, C$_{6-12}$arylC$_{1-3}$alkyl or C$_{6-12}$aryl; C$_{1-6}$alkanoyl (—C(=O)Alk$^1$); sulphonyl (—SO$_3$H) C$_{1-6}$alkylsulphonyl (—SO$_2$Alk$^1$); aminosulphonyl (—SO$_2$NH$_2$); C$_{1-6}$alkylaminosulphonyl (—SO$_2$NHAlk$^1$); C$_{1-6}$dialkylaminosulphonyl (—SO$_2$N(Alk$^1$)$_2$); carboxamido (—CONH$_2$); C$_{1-6}$alkylaminocarbonyl (—CONHAlk$^1$); C$_{1-6}$dialkylaminocarbonyl (—CON(Alk$^1$)$_2$); sulphonylamino (—NHSO$_2$H); C$_{1-6}$alkylsulphonylamino (—NHSO$_2$Alk$^1$); C$_{1-6}$dialkylsulphonylamino (—NSO$_2$(Alk$^1$)$_2$); C$_{1-6}$alkanoylamino (—NHC(=O)Alk$^1$); or C$_{1-6}$alkanoylaminoC$_{1-6}$alkyl (—N(Alk$^1$)C(=O)Alk$^1$); where Alk$^1$ is straight or branched C$_{1-6}$alkylene; and X is —O—, —S—, or —N(R$^5$)—, where R$^5$ is hydrogen or C$_{1-6}$alkyl;

or a salt, solvate, hydrate or N-oxide thereof.

2. A compound according to claim 1 wherein X is —O—.

3. A compound according to claim 1 wherein Y is —OR$^1$, where R$^1$ is substituted or unsubstituted C$_{1-6}$alkyl, said R$^1$ substituent being halogen.

4. A compound according to claim 1 wherein R$^2$ is substituted or unsubstituted C$_{3-8}$cycloalkyl, said R$^2$ substituent being halogen, C$_{1-6}$alkyl, hydroxyl or C$_{1-6}$alkoxy.

5. A compound according to claim 1 wherein R$^3$ is pyrimidinyl or pyridazinyl.

6. A compound of formula (2)

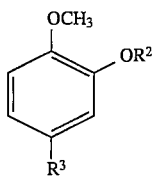

(2)

wherein:

$R^2$ is substituted or unsubstituted $C_{3-8}$cycloalkyl, said $R^2$ substituent being halogen, $C_{1-6}$alkyl, hydroxyl or $C_{1-6}$alkoxy; and $R^3$ is substituted or unsubstituted pyrimidinyl or substituted or unsubstituted pyridazinyl, said $R^3$ substituents being $C_{1-6}$alkyl; $C_{1-6}$alkoxy; $C_{2-6}$alkylenedioxy; $C_{5-7}$cycloalkoxy; haloC$_{1-6}$alkyl; $C_{1-6}$alkylthio; nitro; carboxyl (—CO$_2$H) and carboxyl esterified by $C_{1-6}$alkyl, $C_{6-12}$aryl$C_{1-3}$alkyl or $C_{6-12}$aryl; $C_{1-6}$alkanoyl (—C(=O)Alk$^1$); sulphonyl (—SO$_3$H); $C_{1-6}$alkylsulphonyl (—SO$_2$Alk$^1$); aminosulphonyl (—SO$_2$NH$_2$); $C_{1-6}$alkylaminosulphonyl (—SO$_2$NHAlk$^1$); $C_{1-6}$dialkylaminosulphonyl (—SO$_2$N(Alk$^1$)$_2$); carboxamido (—CONH$_2$); $C_{1-6}$alkylaminocarbonyl (—CONHAlk$^1$); $C_{1-6}$dialkylaminocarbonyl (—CON(Alk$^1$)$_2$); sulphonylamino (—NHSO$_2$H); $C_{1-6}$alkylsulphonylamino (—NHSO$_2$Alk$^1$); $C_{1-6}$dialkylsulphonylamino (—NSO$_2$(Alk$^1$)$_2$); $C_{1-6}$alkanoylamino (—NHC(=O)Alk$^1$); or $C_{1-6}$alkanoylamino$C_{1-6}$alkyl (—N(Alk$^1$)C(=O)Alk$^1$); where Alk$^1$ is straight or branched $C_{1-6}$ alkylene;

or a salt, solvate, hydrate or N-oxide thereof.

7. A compound according to claim 6 wherein $R^2$ is cyclopentyl.

8. A compound according to claim 6 wherein $R^3$ is substituted or unsubstituted 5-pyrimidinyl.

9. A compound of formula (8)

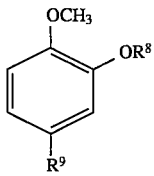

(8)

wherein:

$R^8$ is substituted or unsubstituted cyclopentyl, said $R^8$ substituent being halogen, $C_{1-6}$alkyl, hydroxyl or $C_{1-6}$alkoxy; and $R^9$ is substituted or unsubstituted 5-pyrimidinyl, wherein said $R^9$ substituents are $C_{1-6}$alkyl; $C_{1-6}$alkoxy; $C_{2-6}$alkylenedioxy; $C_{5-7}$cycloalkoxy; haloC$_{1-6}$ alkyl; $C_{1-6}$alkylthio; nitro; carboxyl (—CO$_2$H) and carboxyl esterified by $C_{1-6}$alkyl, $C_{6-12}$aryl$C_{1-3}$alkyl or $C_{6-12}$aryl; $C_{1-6}$alkanoyl (—C(=O)Alk$^1$); sulphonyl (—SO$_3$H); $C_{1-6}$alkylsulphonyl (—SO$_2$Alk$^1$); aminosulphonyl (—SO$_2$NH$_2$); $C_{1-6}$alkylaminosulphonyl (—SO$_2$NHAlk$^1$); $C_{1-6}$dialkylaminosulphonyl (—SO$_2$N(Alk$^1$)$_2$); carboxamido (—CONH$_2$); $C_{1-6}$alkylaminocarbonyl (—CONHAlk$^1$); $C_{1-6}$dialkylaminocarbonyl (—CON(Alk$^1$)$_2$); sulphonylamino (—NHSO$_2$H); $C_{1-6}$alkylsulphonylamino (—NHSO$_2$Alk$^1$); $C_{1-6}$dialkylsulphonylamino (—NSO$_2$(Alk$^1$)$_2$); $C_{1-6}$alkanoylamino (—NHC(=O)Alk$^1$); or $C_{1-6}$alkanoylamino$C_{1-6}$alkyl (—N(Alk$^1$)C(=O)Alk$^1$); where Alk$^1$ is straight or branched $C_{1-6}$alkylene;

or a salt, solvate, hydrate or N-oxide thereof.

10. A compound of claim 9 wherein $R^9$ is substituted or unsubstituted 5-pyrimidinyl.

11. A compound according to claim 8 which is selected from the group consisting of:
5-(3-cyclopentyloxy-4-methoxyphenyl)pyrimidine; and
5-(3-cyclopentyloxy-4-methoxyphenyl)pyrimidine-2-carboxamide.

12. A pharmaceutical composition comprising a compound of formula (1)

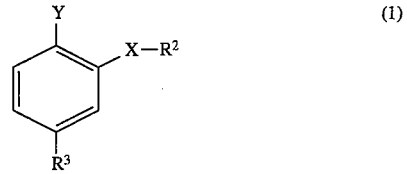

(1)

wherein:

Y is halogen or —OR$^1$, where R$^1$ is substituted or unsubstituted $C_{1-6}$alkyl, said R$^1$ substituent being halogen;

$R^2$ is substituted or unsubstituted $C_{3-8}$cycloalkyl or substituted or unsubstituted $C_{3-8}$cycloalkenyl, said R$^2$ substituents being halogen, $C_{1-6}$alkyl, hydroxyl or $C_{1-6}$alkoxy;

$R^3$ is substituted or unsubstituted pyrimidinyl or substituted or unsubstituted pyridazinyl, said R$^3$ substituents being $C_{1-6}$alkyl; $C_{1-6}$alkoxy; $C_{2-6}$alkylenedioxy; $C_{5-7}$cycloalkoxy; haloC$_{1-6}$alkyl; $C_{1-6}$alkylthio; nitro; carboxyl (—CO$_2$H) and carboxyl esterified by $C_{1-6}$alkyl, $C_{6-12}$aryl$C_{1-3}$alkyl or $C_{6-12}$aryl; $C_{1-6}$alkanoyl (—C(=O)Alk$^1$); sulphonyl (—SO$_3$H); $C_{1-6}$alkylsulphonyl (—SO$_2$Alk$^1$); aminosulphonyl (—SO$_2$NH$_2$); $C_{1-6}$alkylaminosulphonyl (—SO$_2$NHAlk$^1$); $C_{1-6}$dialkylaminosulphonyl (—SO$_2$N(Alk$^1$)$_2$); carboxamido (—CONH$_2$); $C_{1-6}$alkylaminocarbonyl (—CONHAlk$^1$); $C_{1-6}$dialkylaminocarbonyl (—CON(Alk$^1$)$_2$); sulphonylamino (—NHSO$_2$H); $C_{1-6}$alkylsulphonylamino (—NHSO$_2$Alk$^1$); $C_{1-6}$dialkylsulphonylamino (—NSO$_2$(Alk$^1$)$_2$); $C_{1-6}$alkanoylamino (—NHC(=O)Alk$^1$); or $C_{1-6}$alkanoylamino$C_{1-6}$alkyl (—N(Alk$^1$)C(=O)Alk$^1$); where Alk$^1$ is straight or branched $C_{1-6}$alkylene; and X is —O—, —S—, or —N(R$^5$)—, where R$^5$ is hydrogen or $C_{1-6}$alkyl;

or a salt, solvate, hydrate or N-oxide thereof;

together with one or more pharmaceutically acceptable carriers, excipients or diluents.

13. A method for preventing or treating an inflammatory disease in a patient comprising administering to said patient, in combination with a pharmaceutically acceptable carrier, a selective inhibitor of a phosphodiesterase (PDE) IV isoenzyme in an amount sufficient to elevate intracellular levels of adenosine 3',5'-cyclic monophosphate (cAMP), said inhibitor comprising a compound of the formula:

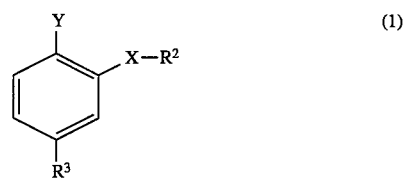

(1)

wherein:

Y is halogen or —OR$^1$, wherein R$^1$ is substituted or unsubstituted $C_{1-6}$alkyl, said R$^1$ substituent being halogen;

R² is substituted or unsubstituted $C_{3-8}$cycloalkyl or substituted or unsubstituted $C_{3-8}$cycloalkenyl, said R² substituents being halogen, $C_{1-6}$alkyl, hydroxyl or $C_{1-6}$alkoxy;

R³ is substituted or unsubstituted pyrimidinyl or substituted or unsubstituted pyridazinyl, said R³ substituents being $C_{1-6}$alkyl; $C_{1-6}$alkoxy; $C_{2-6}$alkylenedioxy; $C_{5-7}$cycloalkoxy; halo$C_{1-6}$alkyl; $C_{1-6}$alkylthio; nitro; carboxyl (—$CO_2H$) and carboxyl esterified by $C_{1-6}$alkyl, $C_{6-12}$aryl$C_{1-3}$alkyl or $C_{6-12}$aryl; $C_{1-6}$alkanoyl (—C(=O)Alk¹); sulphonyl (—$SO_3H$); $C_{1-6}$alkylsulphonyl (—$SO_2$Alk¹); aminosulphonyl (—$SO_2NH_2$); $C_{1-6}$alkylaminosulphonyl (—$SO_2$NHAlk¹); $C_{1-6}$dialkylaminosulphonyl (—$SO_2$N(Alk¹)₂); carboxamido (—$CONH_2$); $C_{1-6}$alkylaminocarbonyl (—CONHAlk¹); $C_{1-6}$dialkylaminocarbonyl (—CON(Alk¹)₂); sulphonylamino (—$NHSO_2H$); $C_{1-6}$alkylsulphonylamino (—$NHSO_2$Alk¹); $C_{1-6}$dialkylsulphonylamino (—$NSO_2$(Alk¹)₂); $C_{1-6}$alkanoylamino (—NHC(=O)Alk¹); or $C_{1-6}$alkanoylamino$C_{1-6}$alkyl (—N(Alk¹)C(=O)Alk¹); where Alk¹ is straight or branched $C_{1-6}$alkylene; and X is —O—, —S—, or —N(R⁵)—, where R⁵ is hydrogen or $C_{1-6}$alkyl;

or a salt, solvale, hydrate or N-oxide thereof.

14. A method according to claim 11 wherein said inflammatory disease comprises asthma.

15. A method according to claim 11 wherein said inflammatory disease is selected from the group consisting of inflammatory airway disease, chronic bronchitis, eosinophilic granuloma, inflammatory arthritis, atopic dermatitis, urticaria, allergic rhinitis, adult respiratory distress syndrome and allergic conjunctivitis.

16. A compound according to claim 11 which is 5-(3-cyclopentyloxy-4-methoxyphenyl)pyrimidine.

17. A compound according to claim 11 which is 5-(3-cyclopentyloxy-4-methoxyphenyl)pyrimidine-2-carboxamide.

18. A pharmaceutical composition comprising, in combination with one or more pharmaceutically acceptable carriers, excipients or diluents, a compound according to claim 16.

19. A method for preventing or treating an inflammatory disease in a patient comprising administering to said patient, in an amount effective to elevate intracellular levels of adenosine 3',5'-cyclic monophosphate (cAMP), a compound according to claim 16.

20. A pharmaceutical composition comprising, in combination with one or more pharmaceutically acceptable carriers, excipients or diluents, a compound according to claim 17.

21. A method for preventing or treating an inflammatory disease in a patient comprising administering to said patient, in an amount effective to elevate intracellular levels of adenosine 3',5'-cyclic monophosphate (cAMP), a compound according to claim 17.

* * * * *

UNITED STATES PATENT AND TRADEMARK OFFICE
CERTIFICATE OF CORRECTION

PATENT NO. : 5,491,147

DATED : February 13, 1996

INVENTOR(S) : Boyd et al.

It is certified that error appears in the above-identified patent and that said Letters Patent is hereby corrected as shown below:

Column 11, line 61, after "5" insert a hyphen -- - --before "Bromo".

Col. 13, line 67, "Example 38)" should be --3a--.

Col. 14, line 26, "(800rag)" should be --(800 mg).

Col. 15, line 15, "thiopone" should be spelled --thiopene--.

Col. 15, line 48, "0,965 g)" should be --0.965 g--.

Col. 20, line 49, "Leukocvtes" should be spelled --Leukocytes--.

UNITED STATES PATENT AND TRADEMARK OFFICE
CERTIFICATE OF CORRECTION

PATENT NO. : 5,491,147
DATED : February 13, 1996
INVENTOR(S) : Boyd et al.

It is certified that error appears in the above-identified patent and that said Letters Patent is hereby corrected as shown below:

Col. 24, claim 12, line 21, "delete the "s" on the beginning of the word --cycloalkyl--.

Col. 24, claim 12, line 22, "delete the "s" on the beginning of the word "cycloalkenyl--.

Col. 25, claim 13, line 1, "delete the "s" on the beginning of the word "cycloalkyl--.

Col. 25, claim 13, line 2, "delete the "s" on the beginning of the word --cycloalkenyl--.

Signed and Sealed this

Twenty-ninth Day of June, 1999

Attest:

Attesting Officer

Q. TODD DICKINSON

Acting Commissioner of Patents and Trademarks